(12) United States Patent
Chambers (10) Patent No.: US 8,828,043 B2
(45) Date of Patent: Sep. 9, 2014

(54) SYSTEMS AND METHODS FOR PREVENTING FORMATION OF BLOOD CLOTS IN THE LEFT ATRIUM

(76) Inventor: Jeffrey W. Chambers, Maple Grove, MN (US)

(*) Notice: Subject to any disclaimer, the term of this patent is extended or adjusted under 35 U.S.C. 154(b) by 117 days.

(21) Appl. No.: 13/157,903

(22) Filed: Jun. 10, 2011

(65) Prior Publication Data

US 2011/0307003 A1  Dec. 15, 2011

Related U.S. Application Data

(60) Provisional application No. 61/353,466, filed on Jun. 10, 2010.

(51) Int. Cl.
*A61M 29/00* (2006.01)
*A61B 17/12* (2006.01)
*A61F 2/24* (2006.01)

(52) U.S. Cl.
CPC ......... *A61F 2/2487* (2013.01); *A61B 17/12122* (2013.01); *A61B 17/12168* (2013.01); *A61F 2250/0067* (2013.01)
USPC ........................................................ 606/200

(58) Field of Classification Search
CPC .................. A61B 17/12122; A61B 17/12099; A61B 2017/3488; A61B 2017/3484; A61F 2/2481; A61F 2/2487
USPC ................... 128/887; 606/191, 194, 200, 213; 600/16, 37
See application file for complete search history.

(56) References Cited

U.S. PATENT DOCUMENTS

| | | | |
|---|---|---|---|
| 2002/0111647 | A1 | 8/2002 | Khairkhahan et al. |
| 2003/0069587 | A1 | 4/2003 | Schorgl et al. |
| 2004/0127935 | A1 | 7/2004 | vanTassel et al. |
| 2005/0038470 | A1 | 2/2005 | van der Burg et al. |
| 2005/0059929 | A1 | 3/2005 | Bolmsjo et al. |
| 2005/0070952 | A1* | 3/2005 | Devellian .................. 606/200 |
| 2006/0020271 | A1 | 1/2006 | Stewart et al. |
| 2006/0224153 | A1 | 10/2006 | Fischell et al. |

(Continued)

FOREIGN PATENT DOCUMENTS

| | | |
|---|---|---|
| WO | 2005/034764 A1 | 4/2005 |
| WO | 2005102181 A1 | 11/2005 |
| WO | 2006052322 A2 | 2/2012 |

OTHER PUBLICATIONS

International Search Report and the Written Opinion (PCT/US2011/039985) dated Dec. 21, 2011 (11 pages).

*Primary Examiner* — Jonathan W Miles
(74) *Attorney, Agent, or Firm* — Dicke, Billig & Czaja, PLLC (57) ABSTRACT

An implantable liner device for preventing formation of blood clots in a left atrium of a patient's heart. The liner device includes a liner body configured, in some embodiments, to cover a portion of an interior surface of the left atrium, the liner body forming a first opening sized for placement about pulmonary vein ostiums of the left atrium and a second opening for fluid alignment with a mitral valve of the left atrium. The liner body can self-expandable from a collapsed state appropriate for percutaneous delivery to the atrium to an expanded state, with the expanded state having a shape appropriate for covering the portion of the interior surface of the left atrium. The liner body can have a cap-like shape, and can be formed of mesh, fabric, braided material, and biological material such as tissue.

10 Claims, 9 Drawing Sheets

(56) References Cited

U.S. PATENT DOCUMENTS

| | | |
|---|---|---|
| 2007/0066993 A1 | 3/2007 | Kreidler |
| 2007/0083230 A1 | 4/2007 | Javois |
| 2007/0208217 A1* | 9/2007 | Walsh et al. .................... 600/37 |
| 2008/0033457 A1 | 2/2008 | Francischelli et al. |
| 2008/0051830 A1 | 2/2008 | Eidenschink et al. |
| 2009/0264982 A1 | 10/2009 | Krause et al. |
| 2010/0185050 A1 | 7/2010 | Alferness et al. |
| 2010/0228335 A1 | 9/2010 | Schorgl et al. |
| 2010/0318166 A1 | 12/2010 | Ransbury |

* cited by examiner

SYSTEMS AND METHODS FOR PREVENTING FORMATION OF BLOOD CLOTS IN THE LEFT ATRIUM

CROSS-REFERENCE TO RELATED APPLICATIONS

This Non-Provisional Patent Application claims the benefit of the filing date of U.S. Provisional Patent Application Ser. No. 61/353,466, filed Jun. 10, 2010, entitled "SYSTEMS AND METHODS FOR PREVENTING FORMATION OF BLOOD CLOTS IN THE LEFT ATRIUM," the entire teachings of which are herein incorporated by reference.

BACKGROUND

The present disclosure generally relates to systems and methods for minimizing formation of blood clots. More particularly, it relates to non-pharmacological systems or device/drug combination systems and methods for preventing blood clot formation in a chamber of a patient's heart or at other anatomical locations, for example preventing atrial thrombi in the left atrium of patients suffering from atrial fibrillation.

Stagnant blood can result in a clot, which is known as a thrombus, while it is immobile at its place of origin. If the clot becomes mobile and is carried away by the blood circulation, it is called an embolus. An embolus proceeds through smaller and smaller arteries until it plugs one of them and prevents blood from flowing any further in that artery. The result can be damage to tissue, and can occur in various parts of the body depending on where the embolus resides. An embolus lodged in an artery of the brain results in a stroke. The formation of a thrombus, movement of the embolus, and clogging of an artery is known as a thromboembolism.

Thromboembolisms can arise under various circumstances, and are an acute concern for patients suffering from atrial fibrillation. Atrial fibrillation is the most common cardiac arrhythmia (i.e., abnormal heart rhythm) and involves the two upper chambers (atria) of the heart. Patients suffering from atrial fibrillation normally have a significantly increased risk of stroke because blood may pool and form clots in the poorly contracting atria, and especially in the left atrial appendage (LAA). The LAA is a small cavity that is connected to the lateral wall of the left atrium (LA) between the mitral valve and root of the left pulmonary vein.

With a normal, healthy heart, the LAA contracts with the remainder of the LA during the cardiac cycle, such that blood within the LAA normally is not stagnant. With atrial fibrillation, however, the LAA (as well as the remainder of the LA) may not contract as expected due to the discoordinated electrical signals. Thus, the LAA is the site of thrombus formation in more than 90 percent of cases of thrombi associated with non-valvular atrial fibrillation. Further, if the LA is enlarged, there is an increased risk and percentage of thrombi that originate in the LA. Moderate to severe mitral regurgitation reduces the risk of stroke for the cases of LA enlargement. The LAA lies in close relation to the free wall of the left ventricle and thus the LAA's emptying and filling, which determines this degree of blood stagnation, may be significantly affected by left ventricular function.

To address the risk of stroke, patients suffering from atrial fibrillation are often administered (oral or systemic) anticoagulants or similar pharmacological therapies. Warfarin is a well-accepted anticoagulant, and is commonly given to atrial fibrillation patients to protect them from stroke. Unfortunately, warfarin (also known as coumadin) has some potential adverse side effects including hemorrhaging. The risk of severe hemorrhaging is small but definite, and any benefit needs to outweigh this risk when warfarin is considered as a therapeutic measure. The risk of bleeding is increased when warfarin is combined with antiplatelet drugs such as aspirin. Additionally, patients must remain vigilant in adhering to the prescribed pharmacological therapy regimen.

In light of the above, a need exists for non-pharmacological systems and methods for preventing formation of blood clots in the left atrium (or other cardiac chamber), especially for patients with atrial fibrillation.

SUMMARY

Some aspects in accordance with principles of the present disclosure relate to an implantable liner device for preventing formation of blood clots in a left atrium of a patient's heart. The liner device includes a liner body configured, in some embodiments, to cover a portion of an interior surface of the left atrium, the liner body forming a first opening sized for placement about pulmonary vein ostiums of the left atrium and a second opening for fluid alignment with a mitral valve of the left atrium. In some embodiments, the liner body is self-expandable from a collapsed state appropriate for percutaneous delivery to the atrium to an expanded state, with the expanded state having a shape appropriate for covering the portion of the interior surface of the left atrium. In related embodiments, the liner body shape is cap-like, for example in the expanded state. In yet other embodiments, the liner body is formed of a mesh, fabric, or braided material, and in other embodiments includes or comprises a biological material such as tissue (e.g., amnion tissue).

DETAILED DESCRIPTION

Figures 1A, 1B, 1C:
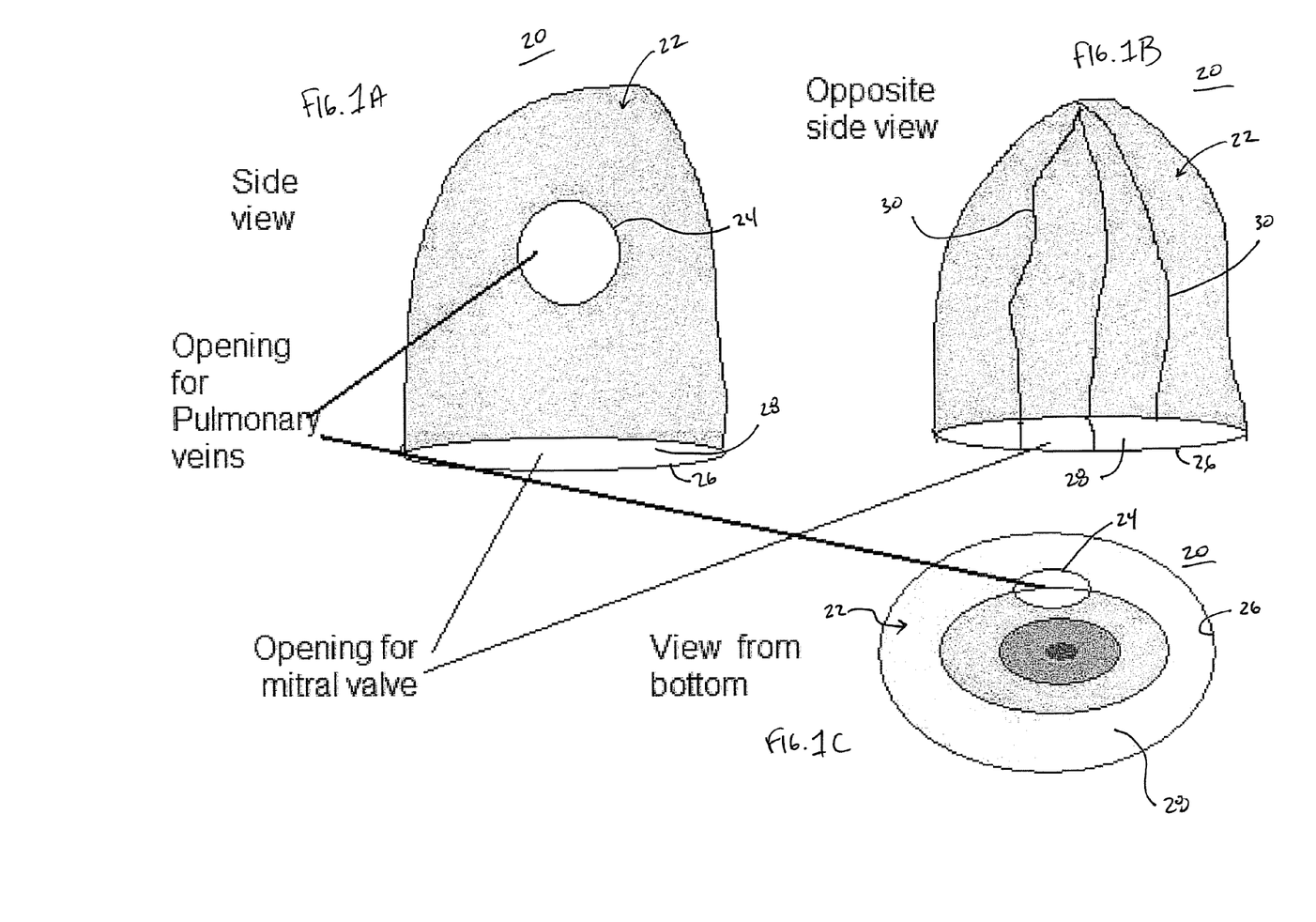
FIG. 1A is a simplified side view of an implantable cardiac chamber liner device in accordance with principles of the present disclosure and configured for implantation within a left atrium.
FIG. 1B is an opposite side view of the liner device of FIG. 1A.
FIG. 1C is a bottom view of the liner device of FIG. 1A.

One embodiment of an implantable liner device 20 in accordance with principles of the present disclosure for preventing cardiac chamber blood clots, such as in the left atrium of a patient, is shown in FIGS. 1A-1C. The liner device 20 includes a liner body 22 that is expandable from a collapsed state (described below) to the expanded state of FIGS. 1A-1C. In the expanded state, the liner body 22 has a cap-like or cup-like shape, configured to match a size, shape, and contour of an interior surface of the cardiac chamber being treated, for example a portion of the interior left atrium. Thus, the liner body 22 serves as a coating or lining on the bodily surface in question, thereby preventing blood clots from forming on the anatomical surface. For reasons made clear below, the liner body 22 forms or defines one or more openings sized and located to accommodate various anatomical structures associated with the chamber surface being treated. For example, with constructions in which the liner device 20 is intended to be implanted in the left atrium, the liner body 22 defines first and second openings 24, 26. In general terms, the first opening 24 is sized in accordance with the pulmonary vein roots or ostiums originating in the left atrium, whereas the second opening 26 is sized in accordance with a mitral valve opening in the left atrium.

The liner body 22 can be formed of various biocompatible materials appropriate for atraumatic contact with cardiac tissue (or other bodily tissue). Further, the liner body 22 has a thin-walled construction to define an open interior region 28 (referenced generally). The openings 24, 26 are fluidly open to the interior region 28. For example, the liner body 22 can be a fabric, polymer, metal mesh, braided material, or other such material having the appropriate properties such as biological material or tissue. For example, amnion tissue can be employed, and can be variously modified or unmodified form of amnion tissue such as non-cryo amnion tissue, solubilized amnion tissue, amnion tissue fabric, chemically modified amnion tissue, amnion tissue treated with radiation, amnion tissue treated with date, or a combination thereof. Materials such as polymer, placental tissue, pericardium tissue, small intestine submucosa can also be used, alone or in combination with the amnion tissue. The tissue can be attached to the inside, the outside, both inside and outside, or complete encapsulation of a scaffolding of the liner body 22. In some constructions, at least part of the covering or lining of the liner body 22 (e.g., as applied to a scaffolding of the liner body 22) comprises a plurality of layers of tissue, such as a plurality of layers of amnion tissue. To prevent blood clot formation, the liner body 22 is coated with an anti-thrombotic material or medication in some embodiments. In other embodiments, the liner body 22 is configured to promote endothealization with cardiac tissue, effectively resulting in a modified heart wall lining. Regardless, in some constructions the liner body 22 is readily collapsible from the expanded state of FIGS. 1A-1C, and can be repeatedly transitioned between the expanded and collapsed states.

In some embodiments, the construction of the liner body 22 inherently provides a self-expanding attribute. For example, where the liner body 22 is a metal mesh or braided metal, the liner body 22 itself will self-expand from the collapsed state to or toward the expanded state. In other embodiments, one or more reinforcing structures 30 (FIG. 1B) can be disposed on or within the liner body 22 material that provide the self-expanding characteristic. The reinforcing structures 30 can be metal wires or braids (e.g., Nitinol) having a shape memory attribute that forces the liner body 22, and thus the liner device 20 as a whole, to or toward the expanded state. In yet other embodiments, the liner body 22 is flexible, and is not self-expanding.

Figure 2:
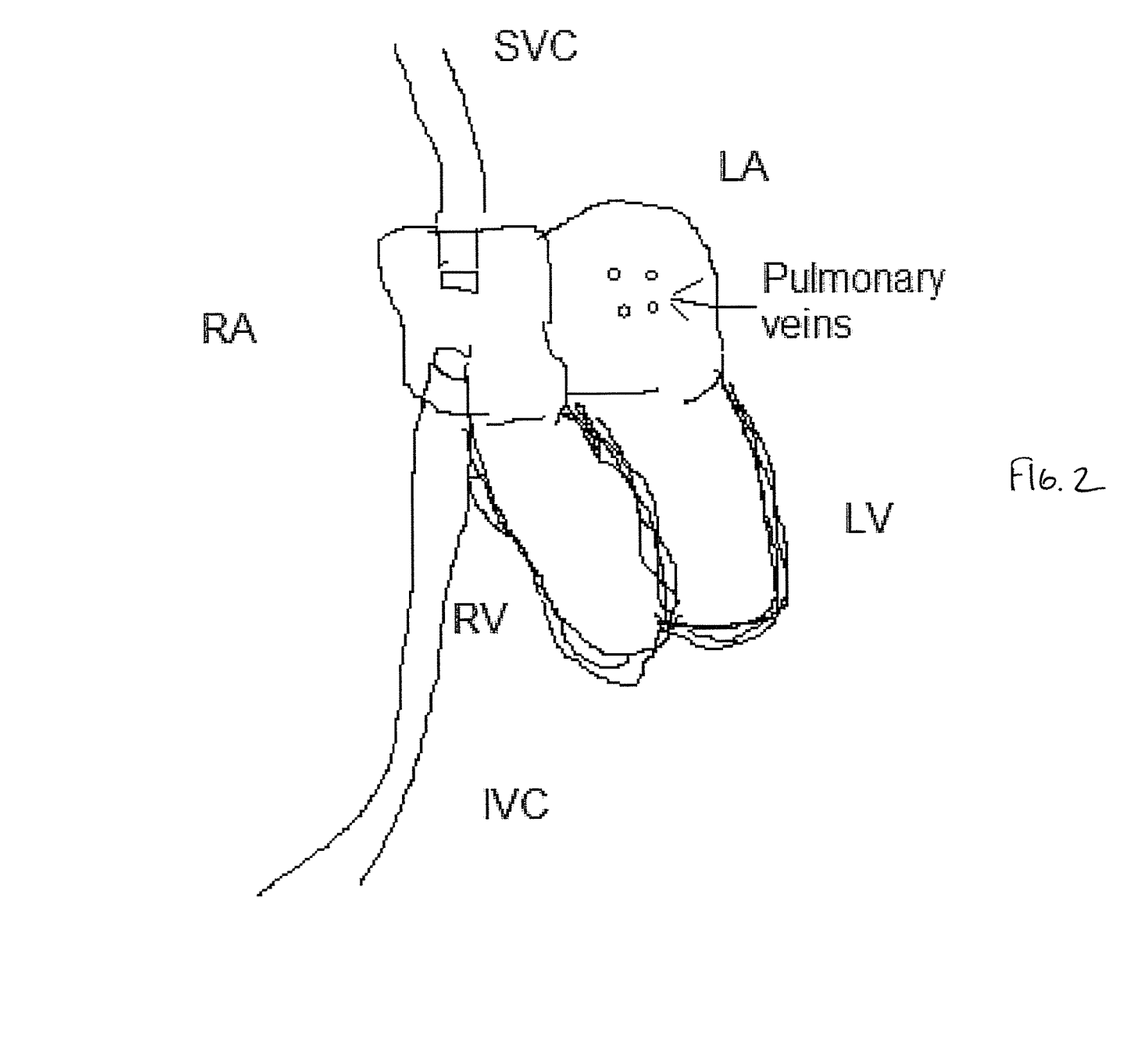
FIG. 2 is a simplified representation of portions of a human heart and related vasculature.
Figure 3:
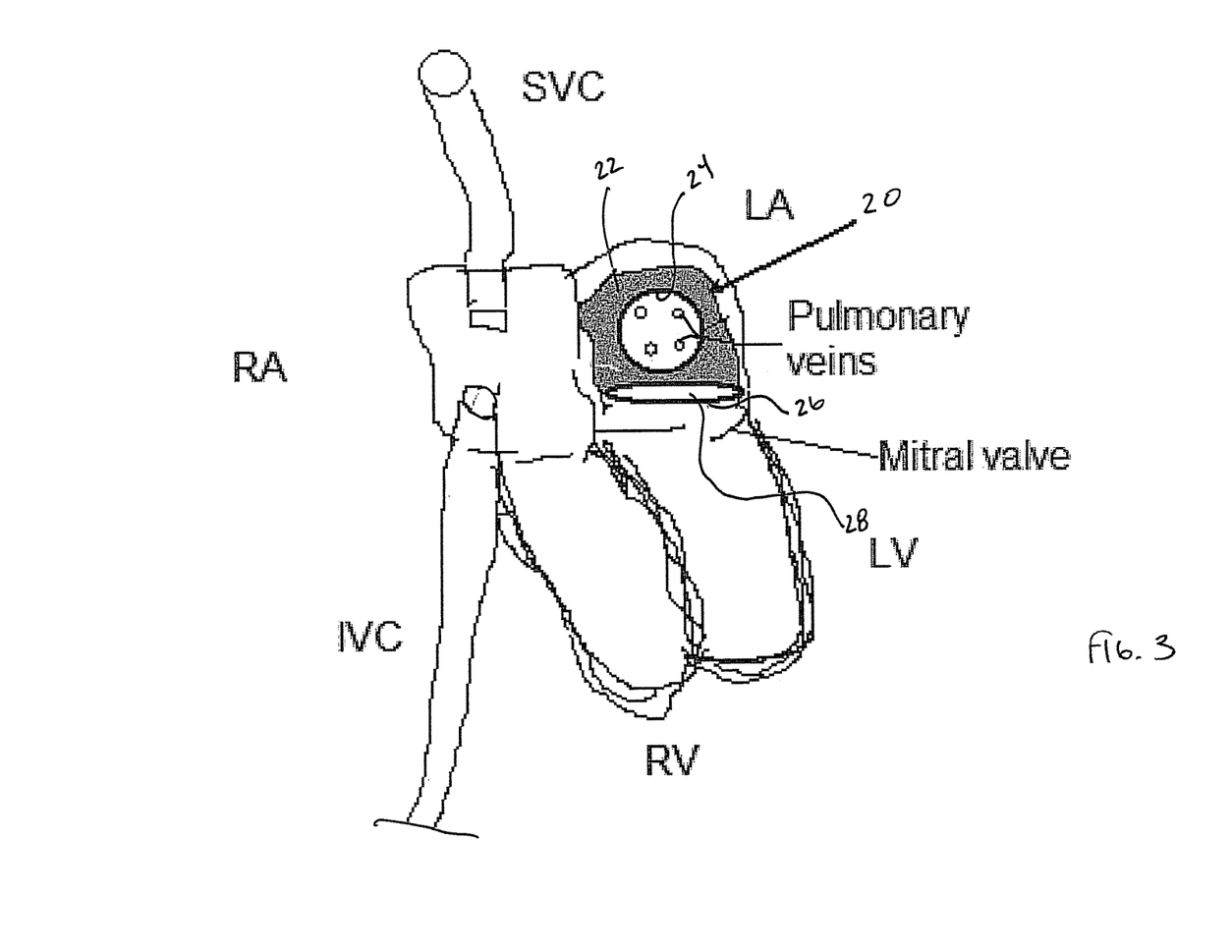
FIG. 3 is a simplified view of the liner device of FIG. 1A implanted within a left atrium portion of the anatomy of FIG. 2.

As indicated above, the cap-like shape of the liner body 22 generally coincides with a size and shape of the interior left atrium in some embodiments. In this regard, FIG. 2 provides a simplified representation of portions of the human heart, including the left atrium (LA). Ostiums or roots of the pulmonary veins originating at the left atrium LA wall are also reflected, as is the mitral valve MV. With the above anatomy of the left atrium LA in mind, FIG. 3 illustrates, in simplified form, final implantation of the liner device 20 within the left atrium LA. As shown, the first opening 24 is aligned with (e.g., circumscribes) the pulmonary vein ostiums or roots. Similarly, the second opening 26 is aligned with (e.g., faces) the mitral valve. A remainder of the liner body 22 is in direct, intimate contact with the interior surface of the left atrium LA. With this arrangement, the liner body 22 prevents the formation of blood clots along the interior surface of the left atrium LA. However, necessary blood flow through the left atrium LA is readily permitted, including through the pulmonary veins via the first opening 24 and through the mitral valve via the second opening 26 (it being understood that blood flows through the open interior region 28 (referenced generally) as well). In light of the thin wall nature of the liner body 22, a volumetric capacity of the left atrium LA is very minimally reduced due to the presence of the liner device 20.

In some embodiments, the liner device 20 is self-retaining relative to the left atrium LA due to an outward or expanding bias of the liner device 20. For example, a size and shape of the liner device 20 in the normal, expanded state of FIGS. 1A-1C is slightly less than the corresponding size and shape of the left atrium LA. As a result, once implanted, the liner device 20 maintains or presents an expandable outward force against the walls of the left atrium LA. An inherent flexibility of the liner body 22 combined with the outward expansion force causes the liner body 22 to mimic or match contours along the surface of the left atrium LA. In some embodiments, a series of differently sized and/or shaped ones of the liner devices 20 can be provided, with the surgeon selecting a desired liner device 20 for implantation based upon an evaluation of the size and shape of the patient's left atrium LA. In other embodiments, one or more tissue anchors or similar structures can be provided that intimately retain the liner device 20 against the interior surface of the left atrium LA.

In some embodiments, the liner device 20 is surgically delivered to the left atrium LA. For example, the liner device 20 can be delivered by a catheter via a vein with a transseptal puncture or in a retrograde fashion through the aortic and mitral valves via an arterial approach. With catheter-based delivery techniques, the liner device 20 is initially forced to the collapsed state of FIG. 4A and slidably inserted within a delivery catheter 40. A proximal end 42 of the liner device 20 is attached to an insertion tool 44 that is similarly slidably disposed within the delivery catheter 40. As a point of reference, in the collapsed state of FIG. 4A, the second opening 26 serves as the distal end of the liner device 20 relative to the insertion tool 44, and is located proximal a distal end 46 of the delivery catheter 40.

To deliver the liner device 20, a sheath can be placed into the right femoral vein. A transseptal puncture is done to allow a transseptal sheath to be placed across the intratrial septum and into the left atrium LA. Next, a wire 50 (or multiple wires) are placed in one (or more) of the pulmonary veins via the transseptal sheath as shown in FIG. 4B. The positioning wire or wires 50 are threaded through the pulmonary vein(s) and into the left atrium LA.

Figure 4A:
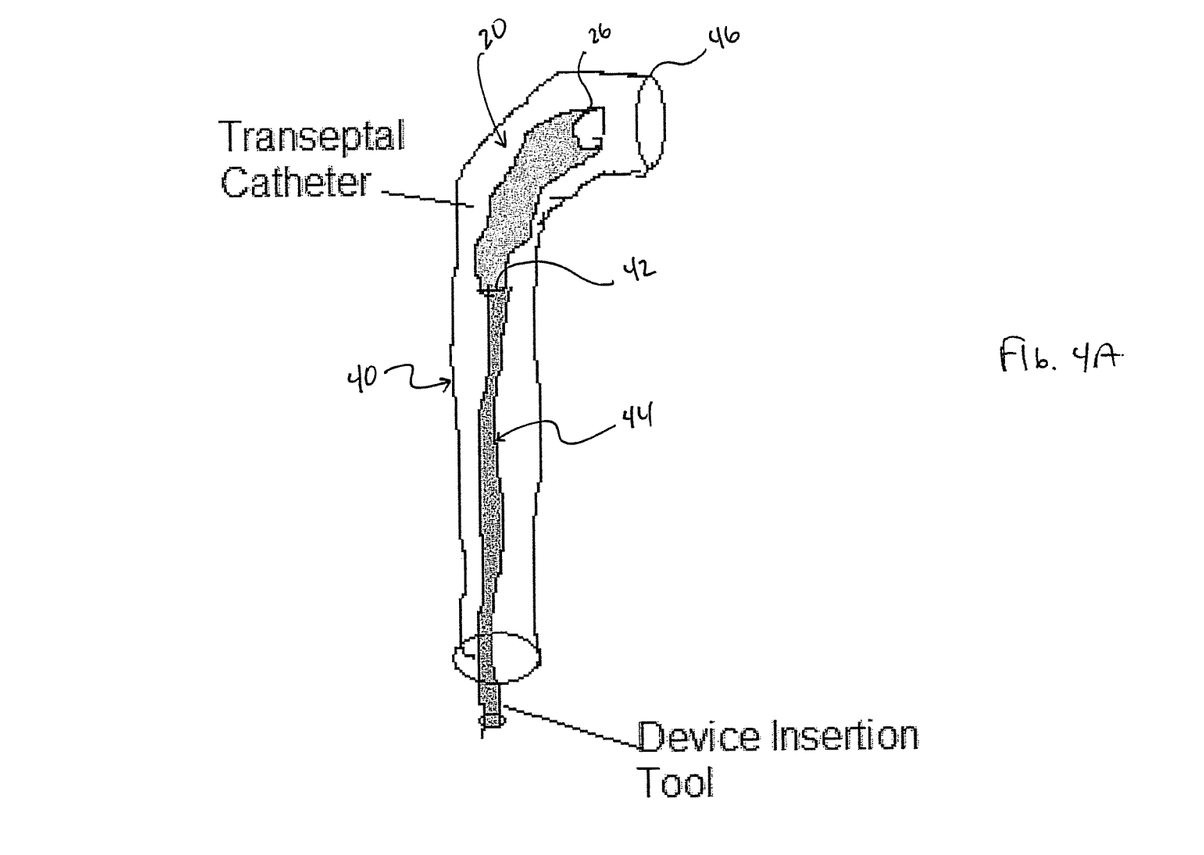
FIGS. 4A-4E illustrate a method of implanting the liner device of FIG. 1A within the left atrium in accordance with methods of the present disclosure.
Figure 4B:
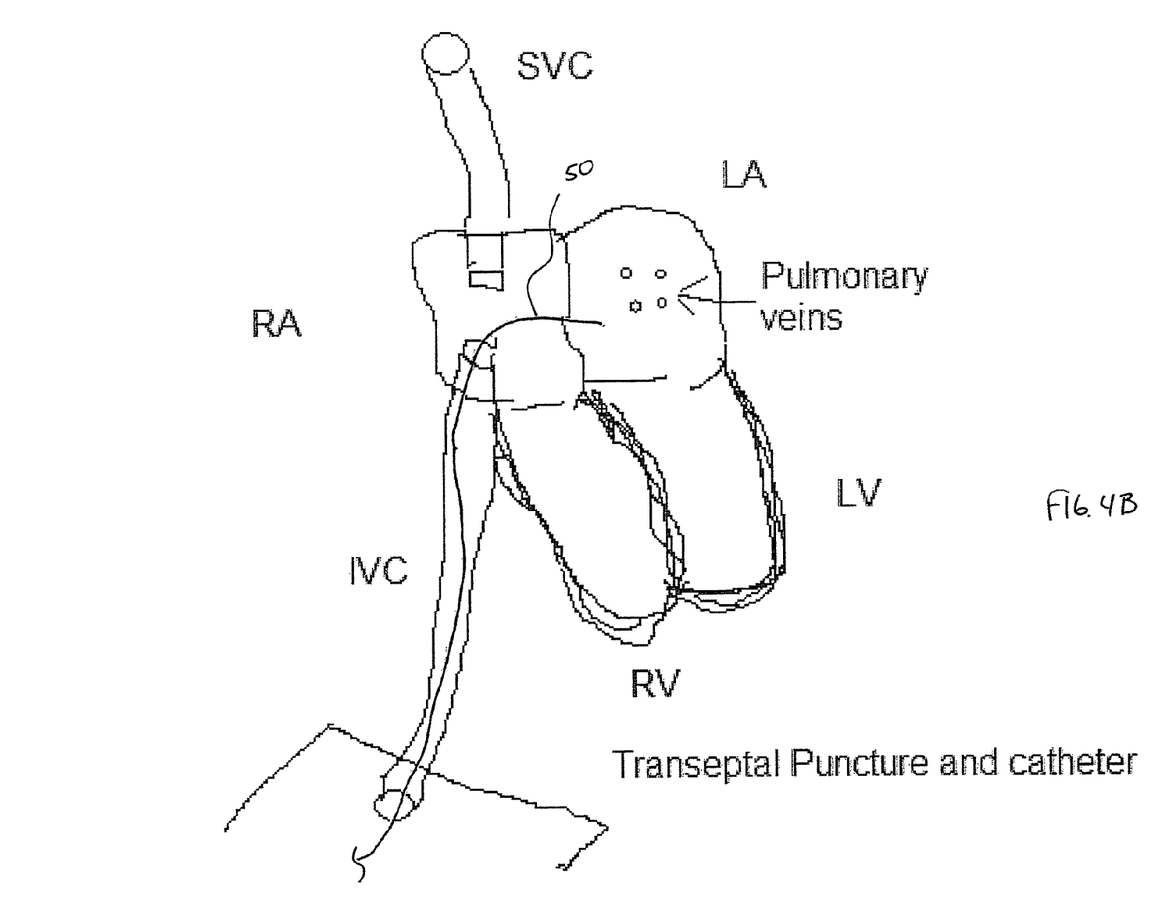
Figure 4C:
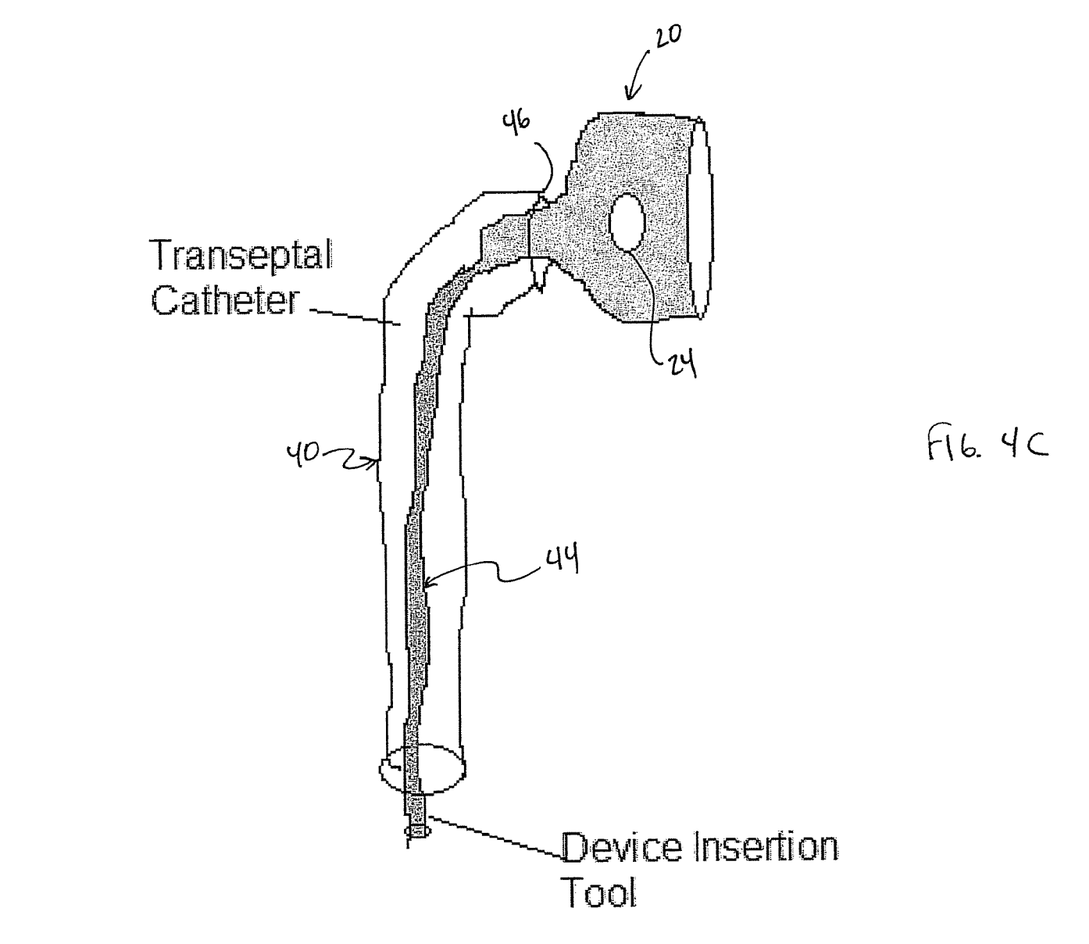
Figure 4D:
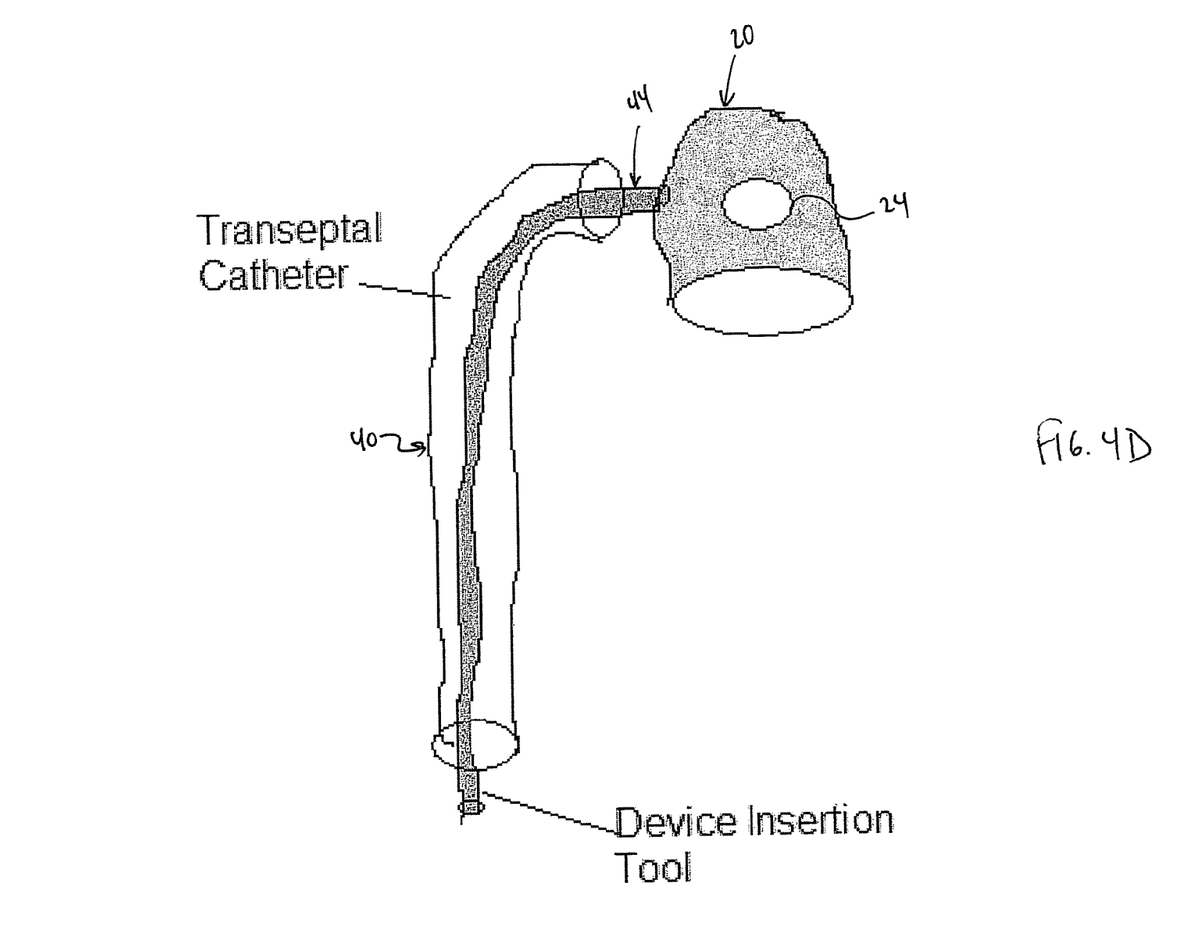
Figure 4E:
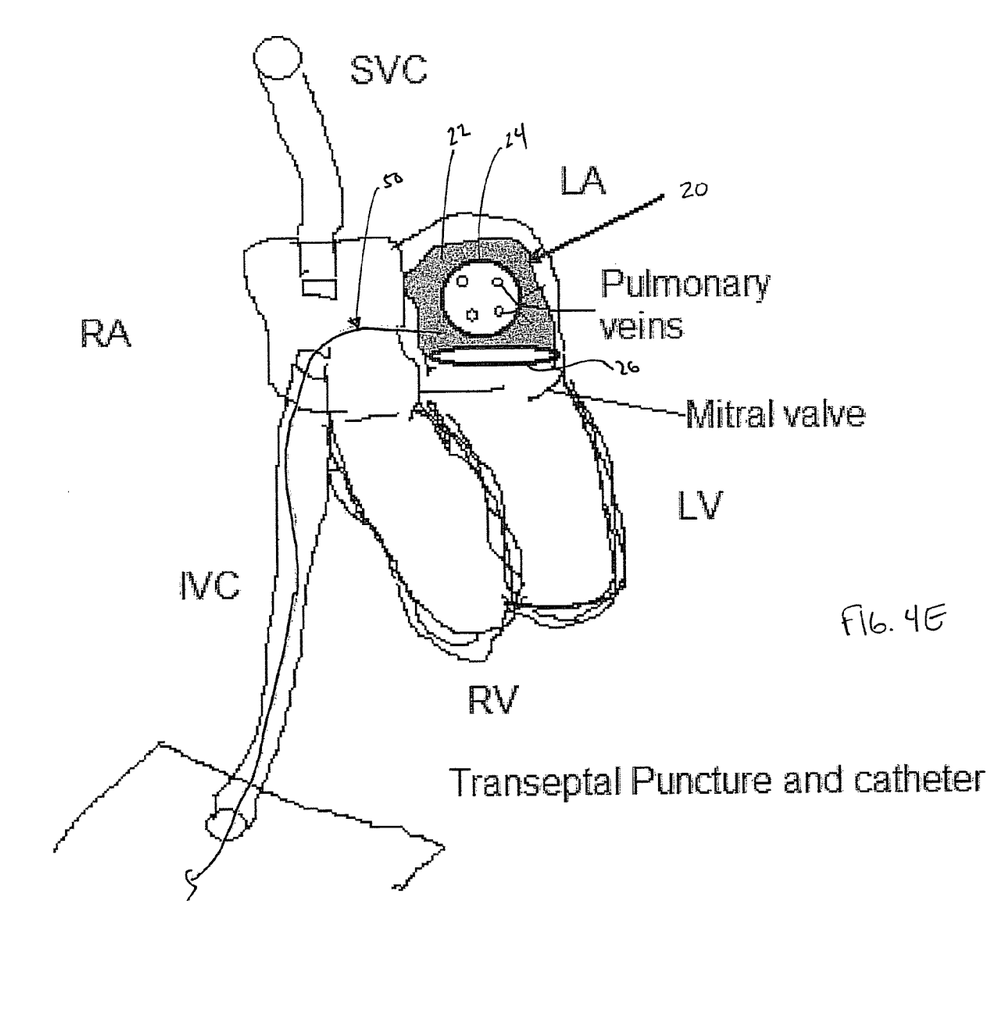

With cross-reference between FIGS. 4A and 4B, the liner device 20 is then loaded in the transseptal delivery catheter 40 as described above, including releasably connecting the liner device 20 to the insertion tool 44. With the liner device 20 in the collapsed state, the delivery catheter 40 is then delivered through the transseptal sheath and into the left atrium LA. With the distal end 46 of the delivery catheter 40 in the left atrium LA, the liner device 20 can then be released. As shown in FIG. 4C, the insertion tool 44 is moved distally relative to the transseptal delivery catheter 40, thereby forcing the liner device 20 distally beyond the distal end 46 of the transseptal delivery catheter 40. Upon being released from the confines of the transseptal catheter 40, the liner device 20 begins to self-expand. In the view of FIG. 4D, the liner device 20 is completely released from the confines of the delivery catheter 40 and has self-assumed the expanded state. In this regard, and with reference to FIG. 4E, the positioning wire(s) 50 otherwise extending through the pulmonary vein(s) permit self-positioning of the liner device 20 relative to the left atrium LA by extending through the first opening 24 in a manner that generally aligns the first opening 24 about the pulmonary vein ostiums/roots. The second opening 26 is naturally aligned with (or faces) the mitral valve. Alternatively, the surgeon can manipulate the liner device 20 to obtain the proper position in which the first opening 24 is aligned with the pulmonary vein ostiums, and the second opening 26 is aligned with (or faces) the mitral valve. For example, positioning of the liner device 20 can be done under commercially available x-ray imaging and with either transesophageal or intracardiac echocardiography.

Once the liner device 20 is in the desired position relative to the left atrium LA, it is released from the insertion tool 44 (FIG. 4D). Releasable coupling between the liner device 20 and the insertion tool 44 can be accomplished with various mechanisms, such as tethers, magnets, etc. The insertion tool 44 and the transseptal delivery catheter 40 (FIG. 4D) are then removed from the patient, as is the transseptal sheath. The implanted liner device 20 functions to minimize or prevent formation of blood clots along the wall(s) of the left atrium LA (or other chamber at which the liner device 20 is implanted). For example, the liner body 20 can be coated with or carry an antithrombotic material, compound, or medication that prevents clots from forming. Alternatively, or in addition, the liner device 20 can endothealize over time (i.e., the lining of the left atrium LA grows over the implanted liner device 20). The resultant, "new" heart wall lining is smooth, unlike the natural lining of the left atrium LA that otherwise has trabeculi. Blood clots are unlikely to form on the smooth, endothealized surface.

Figure 5A:
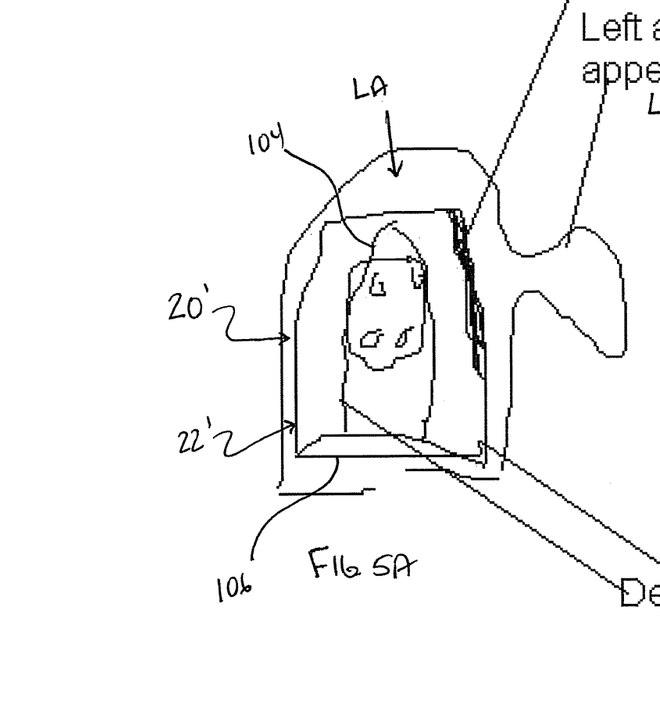
FIGS. 5A and 5B are simplified views of an alternative liner device in accordance with principles of the present disclosure and implanted within a left atrium.
Figure 5B:
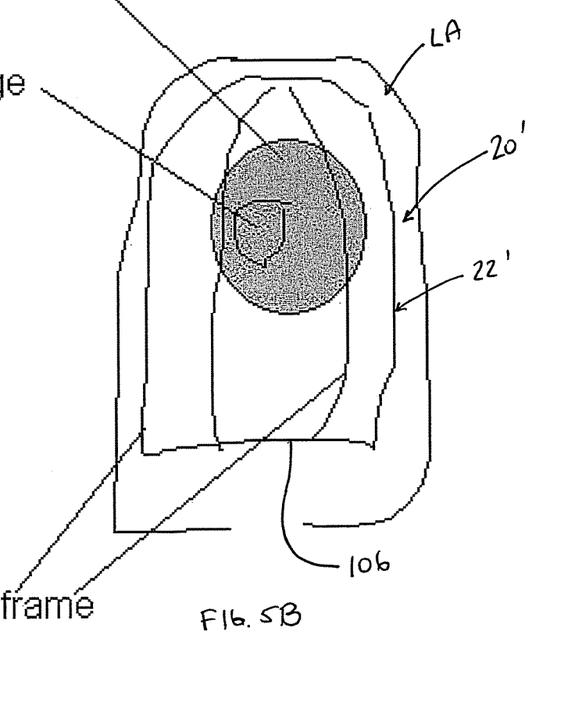

An alternative embodiment liner device 20' in accordance with principles of the present disclosure is shown in FIGS. 5A and 5B, following implantation to the left atrium LA. The liner device 20' is akin to the liner device 20 (FIG. 1A) described above, and includes a liner body 22' comprised of framework or scaffolding 100 and a material coating 102. The framework 100 can assume any of the forms described above, configured and sized (e.g., self-expanding mesh) for placement within and along an interior wall of the left atrium. The framework 100 can further define or form a first opening 104 for placement about the about the pulmonary vein ostiums/roots, as well as a second opening 106 (referenced generally) that is naturally aligned with (or faces) the mitral valve upon final deployment. Regardless, the material coating 102 is applied to only a portion of the framework 100, and is of sufficient size to cover the left atrial appendage (LAA). The material coating 102 can assume any of the forms described above, such as the biological tissues listed previously. The material coating 102 can be maintained by the framework 100 in various fashions, such as by an appropriate, biologically compatible adhesive.

Although the present disclosure has been described with reference to preferred embodiments, workers skilled in the art will recognize that changes can be made in form and detail without departing from the spirit and scope of the present disclosure. For example, the liner device can be configured to modify the interior surface of cardiac chambers other than the left atrium (as well as other organs), and thus can have shapes and/or openings differing from those shown. Along these same lines, other constructions in accordance of the present invention provide the liner device as having a shape differing from the cap-like shape shown, such as a relatively planar sheet.

What is claimed is:

1. An implantable liner device for preventing formation of blood clots in a left atrium of a patient's heart, the device comprising:
   a liner body configured to cover a portion of an interior surface of the left atrium, the liner body having a cup shape defining a closed proximal end and forming a first opening configured for placement about pulmonary vein ostiums of the left atrium and a second opening for fluid alignment with a mitral valve of the left atrium, the first opening being formed through a thickness of the liner body between the closed proximal end and the second opening, wherein the liner device is configured to maintain an expandable outward force against interior walls of the left atrium.

2. The liner device of claim 1, wherein the liner body is configured to self-transition from a collapsed state to an expanded state, the expanded state shaped to cover a portion of an interior surface of the left atrium.

3. The liner device of claim 2, wherein the liner body has the cup shape in the expanded state.

4. The liner device of claim 1, wherein the liner body is formed of a polymer.

5. The liner device of claim 1, wherein the liner body is formed of a metal mesh.

6. The liner device of claim 1, wherein the liner body is formed of a braided material.

7. The liner device of claim 1, wherein the liner body includes biological material.

8. The liner device of claim 1, wherein the liner body is configured to be implanted percutaneously.

9. The liner device of claim 1, wherein the second opening is formed at a distal end of the liner body opposite the closed proximal end.

10. The liner device of claim 1, wherein the liner body is configured to match a size, shape and contour of the interior surface of the left atrium.

* * * * *